(12) United States Patent
Roberts et al.

(10) Patent No.: US 10,342,480 B2
(45) Date of Patent: Jul. 9, 2019

(54) MAGNETOENCEPHALOGRAPHY BIOMARKERS OF GABA-B AGONIST DRUG ACTIVITY IN AUTISM SPECTRUM DISORDERS

(71) Applicant: THE CHILDREN'S HOSPITAL OF PHILADELPHIA, Philadelphia, PA (US)

(72) Inventors: Timothy P. L. Roberts, Avondale, PA (US); James Christopher Edgar, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 746 days.

(21) Appl. No.: 14/776,168

(22) PCT Filed: Mar. 17, 2014

(86) PCT No.: PCT/US2014/030138
§ 371 (c)(1),
(2) Date: Sep. 14, 2015

(87) PCT Pub. No.: WO2014/145382
PCT Pub. Date: Sep. 18, 2014

(65) Prior Publication Data
US 2016/0022207 A1 Jan. 28, 2016

Related U.S. Application Data

(60) Provisional application No. 61/787,077, filed on Mar. 15, 2013.

(51) Int. Cl.
*A61B 5/04* (2006.01)
*A61B 5/00* (2006.01)
(52) U.S. Cl.
CPC ........ *A61B 5/4848* (2013.01); *A61B 5/04009* (2013.01); *A61B 5/4076* (2013.01)
(58) Field of Classification Search
CPC .......... A61B 5/04009; A61B 5/4076; A61B 5/4848
See application file for complete search history.

(56) References Cited

U.S. PATENT DOCUMENTS

2014/0221450 A1* 8/2014 Briault ................. A61K 31/404
514/418

OTHER PUBLICATIONS

Gandal et al., Validating γ oscillations and delayed auditory responses as translational biomarkers of autism, Biol. Psychiatry, 2010, 1100-1106, 68.
Myers et al., Management of Children With Autism Spectrum Disorders, Pediatrics, 2007, 1162-1182, 120.
Roberts et al., MEG Detection of Delayed Auditory Evoked Responses in Autism Spectrum Disorders: Towards an Imaging Biomarker for Autism, Autism Res., 2010, 8-18, 3.
Roberts, Electrophysiological Signatures of Language Impairment in Autism Spectrum Disorders-Biomarkers, Neurobiological Insight and Potential Early Signals of Efficacy: Magnetoencephalographic (MEG) Investigations, Neuropsychopharmacology, 2012, S8, 38.
Roberts et al., Developmental correlation of diffusion anisotropy with auditory-evoked response, Neuroreport, 2009, 1586-91, 20.
Cardy et al., Auditory evoked fields predict language ability and impairment in children, Int. J. Psychophysiol., 2008, 170-5, 68.
Gage, Cortical sound processing in children with autism disorder: an MEG investigation, Neuroreport, 2003, 2047-51, 14.
Stufflebeam et al., A non-invasive method to relate the timing of neural activity to white matter microstructural integrity, Neuroimage, 2008, 710-6, 42.
Gandal et al., Gamma synchrony: towards a translational biomarker for the treatment-resistant symptoms of schizophrenia, Neuropharmacology, 2012, 1504-18, 62.
Roberts et al., Auditory magnetic mismatch field latency: a biomarker for language impairment in autism, Biol Psychiatry, 2011, 263-9, 70.
Rojas et al., Reduced neural synchronization of gamma-band MEG oscillations in first-degree relatives of children with autism, BMC Psychiatry, 2008, 1-9, 8:66.
Wilson et al., Children and adolescents with autism exhibit reduced MEG steady-state gamma responses, Biol Psychiatry, 2007, 192-7, 62.
Roberts et al., Electrophysiological signatures: magnetoencephalographic studies of the neural correlates of language impairment in autism spectrum disorders, Int J Psychophysiol. 2008, 149-60, 68.
Roberts et al., Maturational differences in thalamocortical white matter microstructure and auditory evoked response latencies in autism spectrum disorders, Brain Res., 2013, 79-85, 1537.
Edgar et al., Neuromagnetic oscillations predict evoked-response latency delays and core language deficits in autism spectrum disorders, J Autism Dev Disord., 2015, 395-405, 45.
Roberts et al., Artemis 123: development of a whole-head infant and young child MEG system, Front Hum Neurosci., 2014, 1-10, 8:99.

\* cited by examiner

*Primary Examiner* — Ruth S Smith
(74) *Attorney, Agent, or Firm* — Robert C. Netter, Jr.; Dann, Dorfman, Herrell & Skillman

(57) ABSTRACT

Methods for screening for therapies against autism spectrum disorders and methods for determining whether a subject would be responsive to a therapy against an autism spectrum disorder are disclosed.

14 Claims, 13 Drawing Sheets

MAGNETOENCEPHALOGRAPHY BIOMARKERS OF GABA-B AGONIST DRUG ACTIVITY IN AUTISM SPECTRUM DISORDERS

This application is a § 371 application of PCT/US2014/030138, filed Mar. 17, 2014, which claims priority under 35 U.S.C. § 119(e) to U.S. Provisional Patent Application No. 61/787,077, filed on Mar. 15, 2013. The foregoing applications are incorporated by reference herein.

This invention was made with government support under Grant No. R01-DC008871 awarded by the National Institutes of Health. The government has certain rights in the invention.

FIELD OF THE INVENTION

The present invention relates to the field of diagnosing neurological disorders, particularly autism spectral disorders.

BACKGROUND OF THE INVENTION

Several publications and patent documents are cited throughout the specification in order to describe the state of the art to which this invention pertains. Each of these citations is incorporated herein by reference as though set forth in full.

Magnetoencephalography (MEG) studies examining superior temporal gyrus (STG) auditory activity in individuals with Autism Spectrum Disorders (ASD) almost uniformly report abnormalities. For example, in the time-domain, several studies have reported delays in the latency of auditory-evoked response peaks in autism, especially that of the 100 ms (M100) STG auditory response (Gage et al. (2003) Neuroreport., 14:2047-51; Roberts et al. (2010) Autism Res., 3:8-18). Although delayed responses have been hypothesized to contribute to language deficits in ASD, there is no clear mechanistic support for such a relationship (Oram Cardy et al. (2008) Int. J. Psychophysiol., 68:170-5; Roberts et al. (2008) Int. J. Psychophysiol., 68:149-60). Emerging evidence also suggests impairments in auditory oscillatory activity in ASD. Presenting 40 Hz click trains to children with autism and age-matched controls, decreased left-hemisphere 40 Hz steady-state gamma band activity was observed in autism (Wilson et al. (2007) Biol. Psychiatry 62:192-7). Presenting 1000 Hz tones and examining the early STG transient gamma-band response, decreased left and right 40 Hz inter-trial coherence (ITC, also called phase-locking factor) in adults with autism as well as in the parents of children with autism was observed, leading to the argument for a deficit in autism in the ability to time gamma oscillations to external stimuli (Rojas et al. (2008) BMC Psychiatry, 8:66).

It is unknown whether a delayed M100 response and decreased auditory gamma activity reflect a single abnormality or if the two abnormalities are distinct. In addition, previous auditory time-frequency studies have focused exclusively on gamma-range activity (~30 to 50 Hz). The motivation for this is likely due to (1) the association between inhibitory interneuron processes and gamma activity (Bibbig et al. (2002) J. Neurophysiol., 88:1634-54; Whittington et al. (2000) Int. J. Psychophysiol., 38:315-36), and (2) a hypothesized inhibitory interneuron dysfunction in ASD (Casanova et al. (2002) J. Child Neurol., 17:692-5; Uhlhaas et al. (2007) Biol. Psychiatry, 62:190-1). High frequency activity, however, is not the only, or even the primary, component of auditory evoked responses, and many studies show a coupling of low- and high-frequency activity such that high-frequency abnormalities are likely associated with low-frequency abnormalities (Canolty et al. (2010) Trends Cogn. Sci., 14:506-15; Lakatos et al. (2004) Brain Res. Cogn. Brain Res., 19:1-9). Studies observing low-frequency resting-state abnormalities in ASD also indicate the need to assess oscillatory processes pre- and post-stimulus across a broad range of frequencies in order to fully characterize neural abnormalities in ASD (Cantor et al. (1986) J. Autism Dev. Disord., 16:169-87; Murias et al. (2007) Biol. Psychiatry, 62:270-3).

SUMMARY OF THE INVENTION

In accordance with the instant invention, methods of diagnosing a neurological disorder, particularly an autism spectrum disorder, in a subject are provided. In a particular embodiment, the method comprises measuring brain activity in the subject by magnetoencephalography after administering a stimulus (e.g., an audio stimulus) to the subject. In a particular embodiment, the 50 and/or 100 ms latency is measured. In a particular embodiment, the brain activity (e.g., latency) is measured in the right hemisphere. An increase in the delay of the response in the subject compared to a normal subject indicates that the subject has the neurological disorder. In a particular embodiment, the stimulus elicited activity in the gamma frequency is measured (e.g., the inter trial coherence or steady state gamma power is measured). A decrease in the stimulus elicited activity in the gamma frequency in the subject compared to a normal subject indicates that the subject has the neurological disorder.

In accordance with another aspect of the instant invention, methods of screening drug candidates for the treatment of a neurological disorder, particularly an autism spectrum disorder, are provided. In a particular embodiment, the method comprises administering a compound to a subject and subsequently measuring brain activity in the subject by magnetoencephalography after administering a stimulus (e.g., an audio stimulus) to the subject. In a particular embodiment, the brain activity (e.g., latency) is measured in the right hemisphere. A modulation in the brain activity after administration of the compound indicates the compound's activity against the neurological disorder. For example, a decrease in the delay in the 50 and/or 100 ms response compared to that observed prior to administration of the compound (baseline) indicates that the compound is therapeutic against the neurological disorder. Similarly, an increase in the stimulus elicited activity in the gamma frequency band compared to that observed prior to administration of the compound (baseline) indicates that the compound is therapeutic against the neurological disorder.

DETAILED DESCRIPTION OF THE INVENTION

Figure 1A:
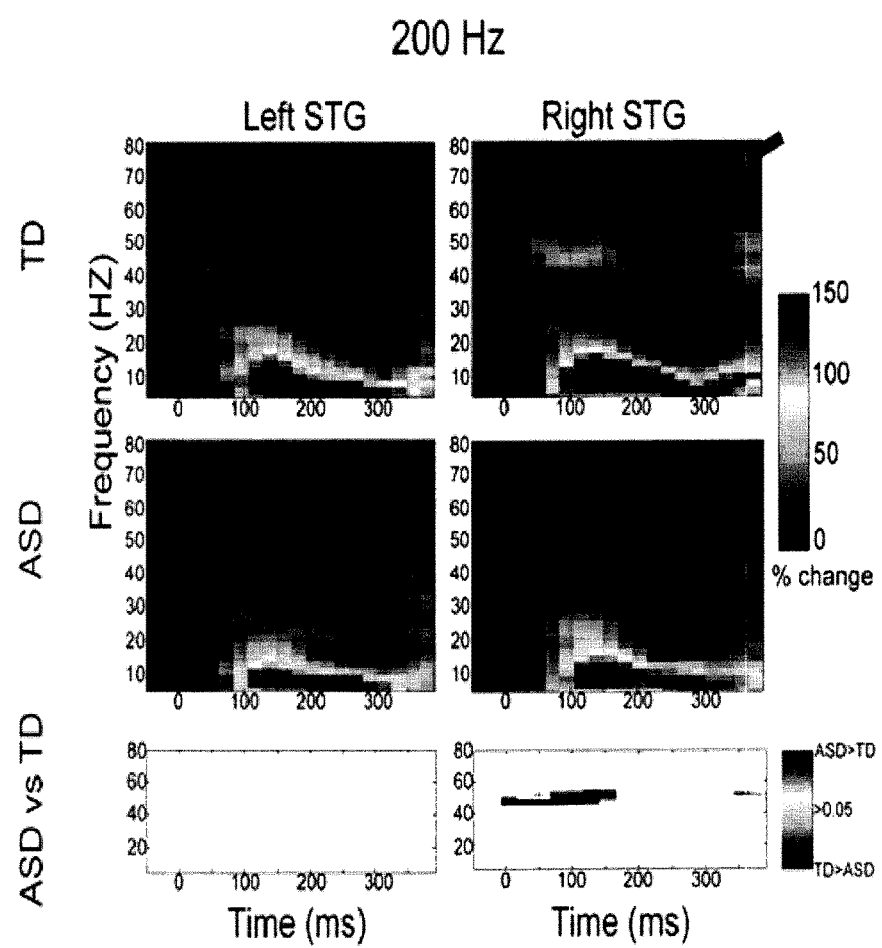
FIG. 1 shows evoked activity and family wise-corrected p-value plots comparing typically developing (TD) and ASD for each frequency. TD>ASD differences are shown in blue, ASD>TD differences in red. Arrows show examples of where greater evoked gamma activity was observed in TD than ASD.
Figure 1B:
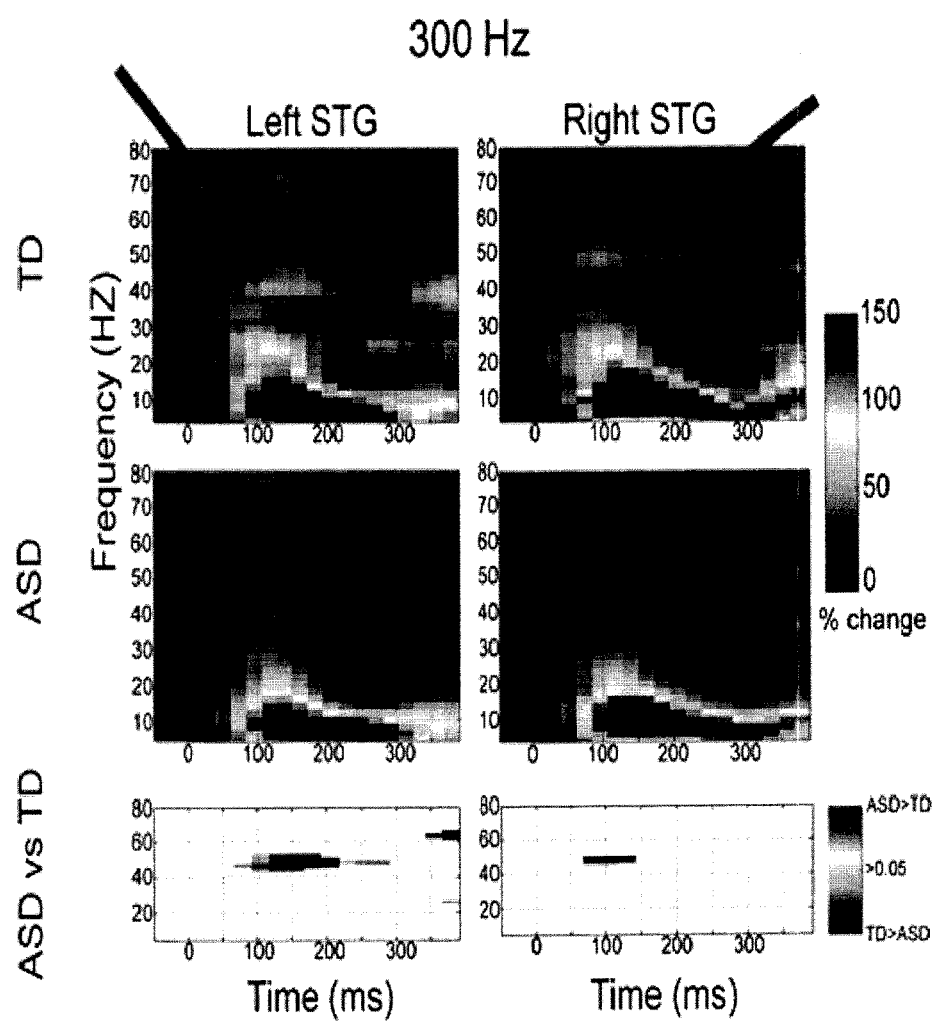
Figure 1C:
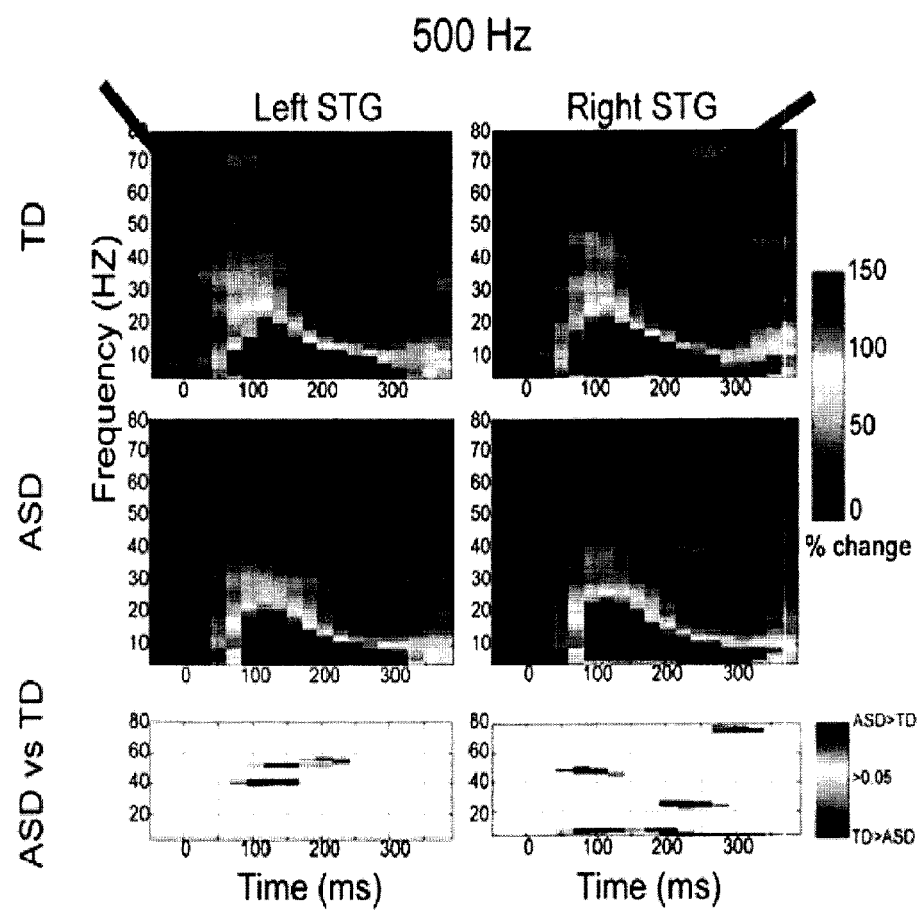
Figure 1D:
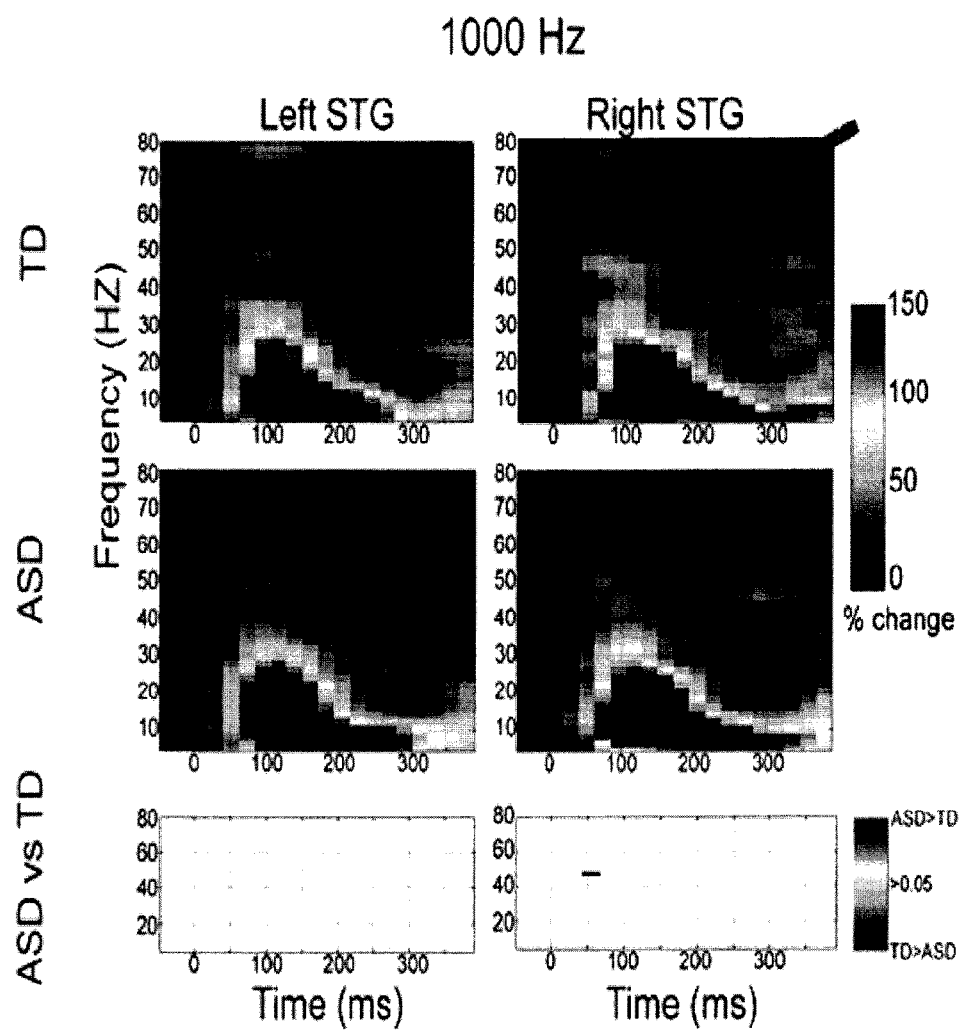
Figure 2A:
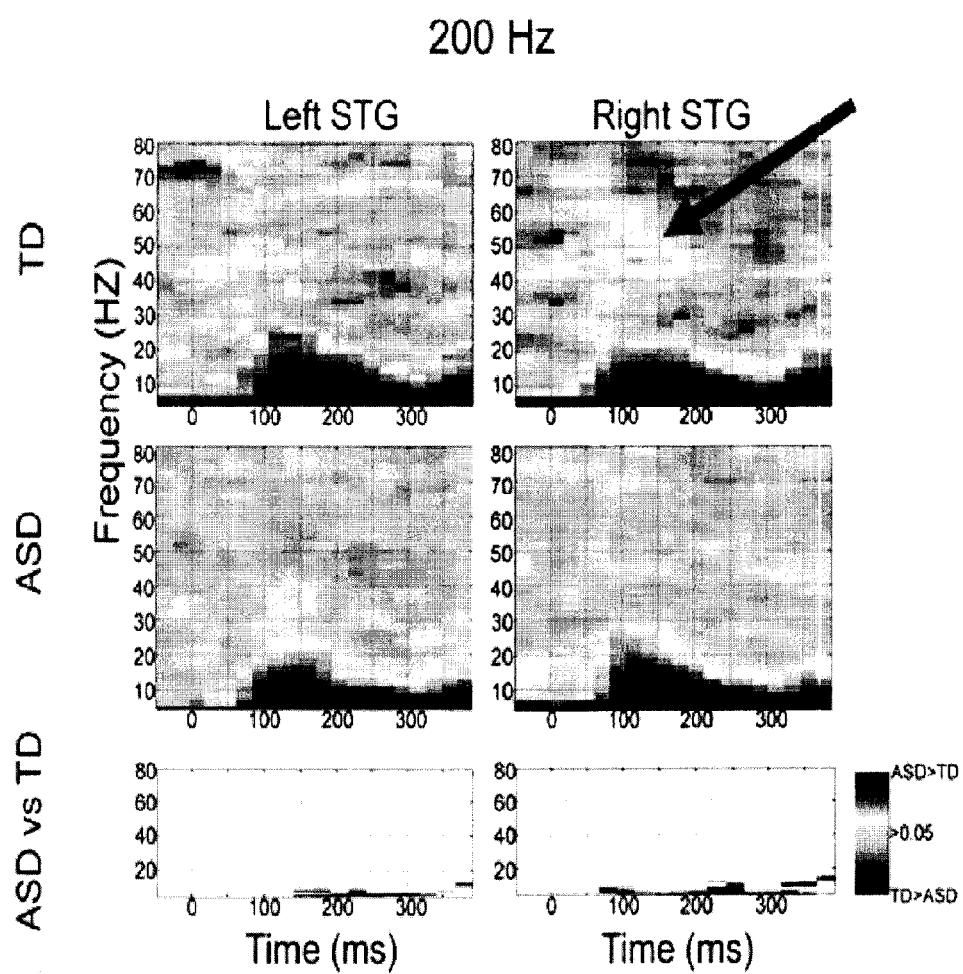
FIG. 2 shows ITC activity and familywise-corrected p-value plots comparing TD and ASD for each frequency. In the grand average maps, ITC values were log transformed to highlight activity at higher frequencies. TD>ASD differences are shown in blue, ASD>TD differences in red. Red arrows show examples of where greater ITC gamma activity was observed in TD than ASD FIG. 3 provides a scatterplot of CELF-4 Core Language Index scores (x axis) and right STG pre-stimulus gamma activity (y axis; 30 to 50 Hz) in individuals with ASD. In ASD, lower CELF-4 scores were associated with increased right-hemisphere pre-stimulus gamma activity.
Figure 2B:
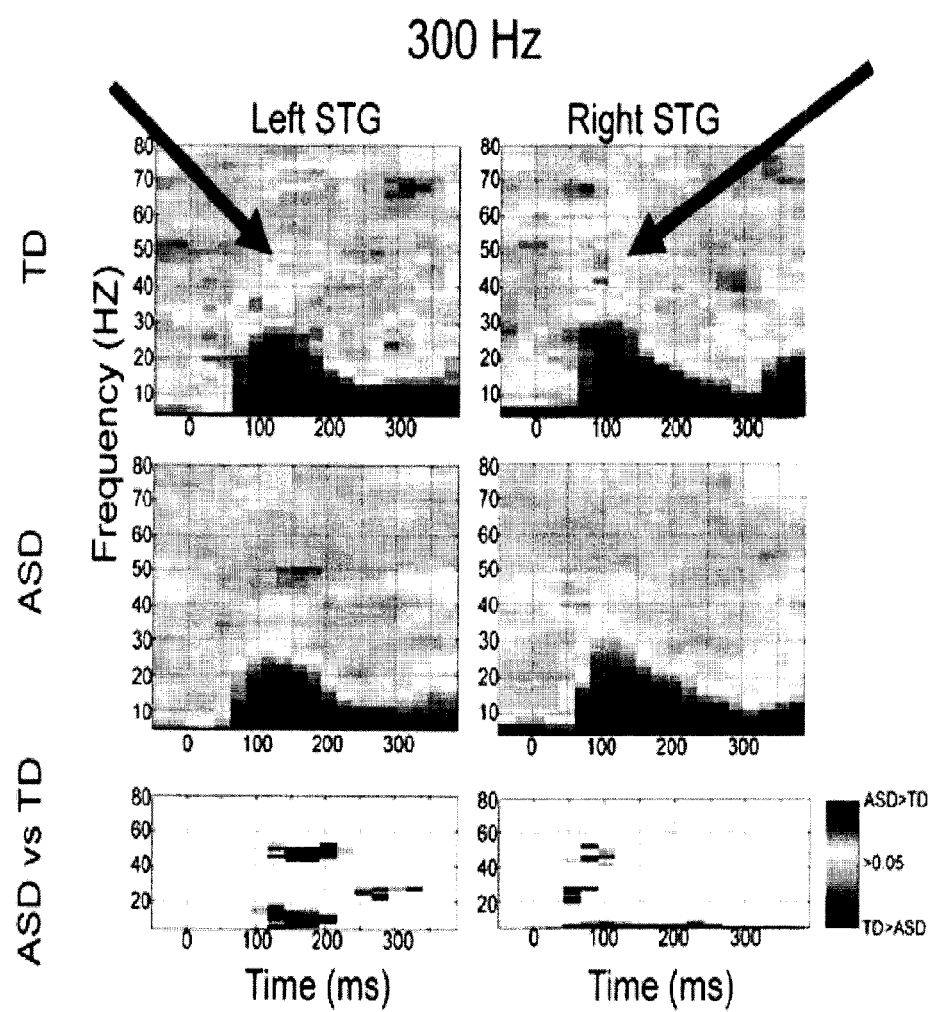
Figure 2C:
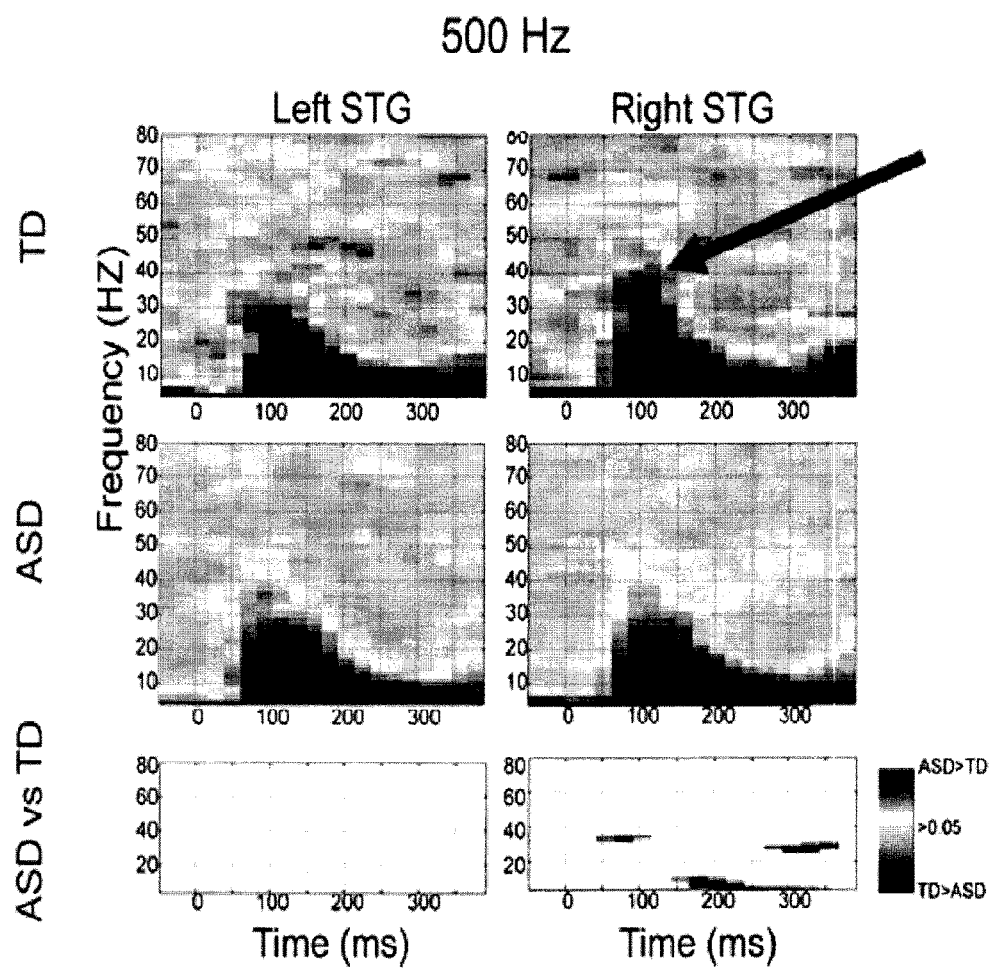
Figure 2D:
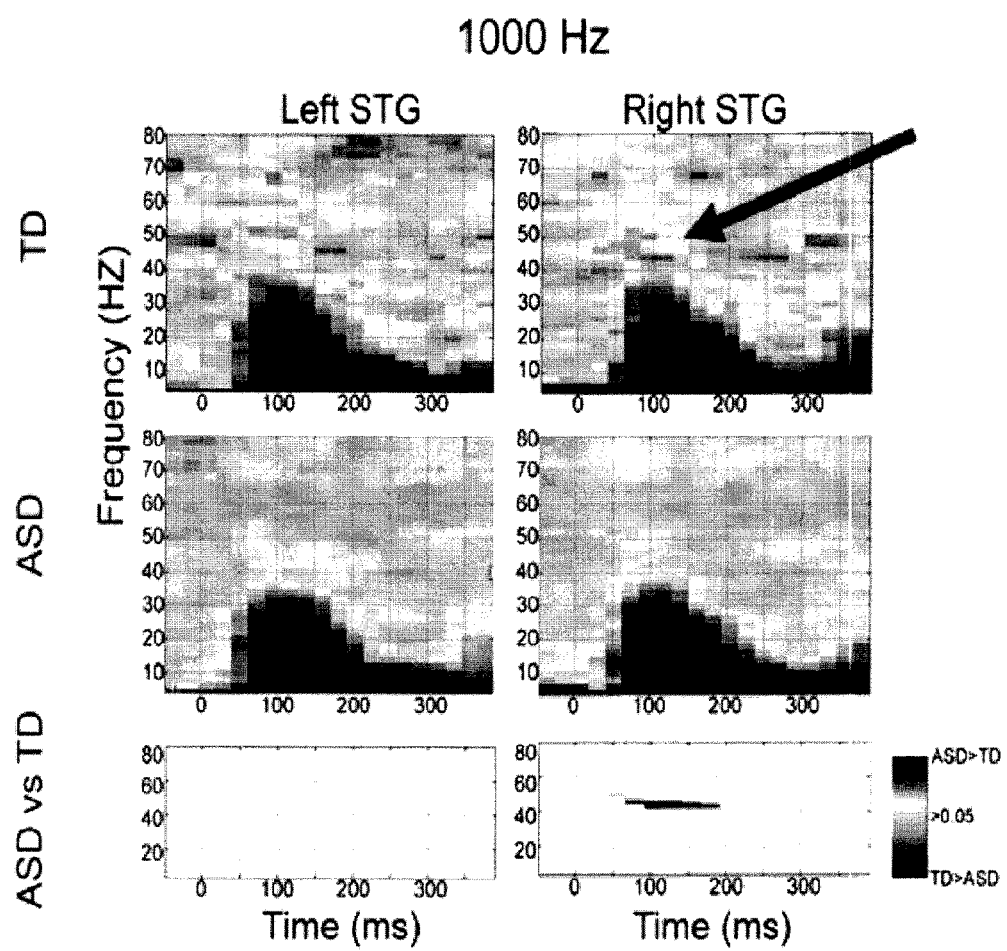

Herein, source-localized STG time-domain and time-frequency activity (evoked and ITC) to transient sinusoidal tones was examined in a large sample of children with ASD and age-matched TD controls. The following hypotheses were tested: (1) Children with ASD would show delayed right-hemisphere M100 STG responses. (2) Based on gamma findings (Wilson et al. (2007) Biol. Psychiatry 62:192-7; Rojas et al. (2008) BMC Psychiatry, 8:66), children with ASD would show decreased early evoked gamma activity and ITC. (3) Post-stimulus gamma band and M100 latency abnormalities would be related, with decreased early evoked gamma activity predicting later M100 responses. (4) Pre-stimulus and post-stimulus oscillatory abnormalities other than gamma-band abnormalities would be observed. (5) Finally, as some studies suggest a relationship between impaired auditory processing and language abilities (Oram Cardy et al. (2008) Int. J. Psychophysiol., 68:170-5; Roberts et al., Auditory Magnetic Mismatch Field Latency: A Biomarker for Language Impairment in Autism. Biol Psychiatry, 2011), STG abnormalities were predicted to be related to performance on a test of language ability. As associations between STG auditory measures and age have been observed, changes in these measures across development were assessed as well as associations between age and STG M100 latency and time-frequency measures.

Here, subjects were presented pure tones at 200, 300, 500, and 1000 Hz while magnetoencephalography (MEG) assessed activity in STG auditory areas in a sample of 105 children with ASD and 36 typically developing controls (TD). The findings revealed a profile such that auditory STG processes in ASD were characterized by pre-stimulus abnormalities across multiple frequencies, then early high-frequency abnormalities followed by low-frequency abnormalities. Increased pre-stimulus activity was a 'core' abnormality, with pre-stimulus activity predicting post-stimulus neural abnormalities, group membership, and clinical symptoms (CELF-4 Core Language Index (CLI)). Accordingly, deficits in synaptic integration in the auditory cortex are associated with oscillatory abnormalities in ASD as well as patient symptoms. Increased pre-stimulus activity in ASD likely demonstrates a fundamental signal-to-noise deficit in individuals with ASD, with elevations in oscillatory activity suggesting an inability to maintain an appropriate 'neural tone' and an inability to rapidly return to a resting state prior to the next stimulus.

The results presented herein demonstrate that right-hemisphere M100 STG 500 Hz responses were approximately 10 ms delayed in ASD. Further, decreased post-stimulus STG~40 Hz evoked activity and ITC was observed bilaterally in children with ASD. As the above latency and gamma abnormalities were unrelated, indicating that these two abnormalities are somewhat distinct (e.g., gamma but not M100 latency group differences in the left hemisphere). Oscillatory abnormalities other than post-stimulus gamma abnormalities were observed in ASD. In particular, in addition to pre-stimulus abnormalities, evoked and ITC low-frequency (below ~20 Hz) group differences were observed.

A striking finding in the present study was the pre-stimulus group difference (left and right hemisphere, 4 to 80 Hz). In addition to robustly differentiating groups, increased pre-stimulus activity predicted M100 latencies in both groups. Other findings also pointed to pre-stimulus activity as a measure warranting additional study: (1) higher 30 to 50 Hz right hemisphere pre-stimulus activity (total power) was associated with lower CELF-4 Core Language Index scores, and (2) although age was associated with pre-stimulus measures, group differences in left hemisphere pre-stimulus activity (4 to 80 Hz) remained even after removing variance in pre-stimulus activity associated with age.

Greater pre-stimulus activity in ASD than TD likely indicates a fundamental signal-to-noise deficit in individuals with ASD. In particular, elevations in oscillatory activity observed in the present study across a broad range of frequencies (and also observed in resting state studies) suggest an inability to maintain an appropriate 'neural tone' and perhaps also an inability to rapidly return to a resting state prior to the next stimulus. Multiple factors likely account for the elevated background activity in ASD. For example, considering gamma activity, it has been demonstrated that NMDAR antagonists (including ketamine, MK-801, and PCP) produce a dose-dependent increase in baseline gamma power using in vivo LFP and EEG recordings in awake rodents (Ehrlichman et al. (2009) Neuroscience, 158:705-12; Hakami et al. (2009) PLoS One, 4: e6755; Lazarewicz et al. (2010) J Cogn Neurosci, 22:1452-64; Leung, L. W. (1985) Electroencephalogr Clin Neurophysiol, 60:65-77; Ma et al. (2000) Behav Brain Res, 111:1-11; Ma et al. (2007) Psychopharmacology (Berl), 191:961-74; Pinault, D. (2008) Biol Psychiatry, 63:730-5). The increase in gamma power associated with NMDAR antagonists is likely associated with reduced GABA release onto pyramidal neurons, as a number of studies have demonstrated dysfunction of interneurons and elevated pyramidal cell activity following NMDAR blockade (Belforte et al. (2010) Nat Neurosci, 13:76-83; Jackson et al. (2004) Proc Natl Acad Sci USA, 101:8467-72; Santana et al. (2011) Biol Psychiatry, 69:918-27).

In line with this, it has recently been shown that fast-spiking interneurons expressing the calcium binding protein parvalbumin and acting through ionotropic GABA(A)-receptors are both necessary and sufficient to generate stimulus-evoked gamma-synchrony in vivo (Sohal et al. (2009) Nature, 459:698-702; Cardin et al. (2009) Nature, 459:663-7). In ASD, a growing body of research has shown GABA receptors to be downregulated in ASD (Fatemi et al. (2009) J Autism Dev Disord., 39:223-30), and ASD participants have shown decreased gamma-band oscillatory activity compared to controls (Orekhova et al. (2007) Biol Psychiatry, 62:1022-9). Interneurons defined by the fast-spiking phenotype and expression of the calcium-binding protein parvalbumin have been implicated in gamma oscillations (Tamas et al. (2000) Nat Neurosci, 3:366-71; Whittington et al. (1995) Nature 373:612-5), and in vivo mouse studies show that inhibiting parvalbumin interneurons suppresses gamma oscillations whereas driving these interneurons is sufficient to generate emergent gamma oscillations (Sohal et al. (2009) Nature, 459:698-702). With regard to the pre-stimulus group differences observed in the present study, it is worth noting that optogenetic inhibition of fast-spiking interneurons reduced stimulus-evoked gamma synchrony and also caused an increase in baseline LFP power in the absence of a stimulus (Sohal et al. (2009) Nature, 459:698-702).

With regard to the functional significance of the post-stimulus gamma abnormalities in ASD, a recent report using high-density intracortical array recordings demonstrated that synaptic integration within the primary auditory cortex is augmented specifically at the gamma oscillation frequency during passive listening (Rubenstein et al. (2003) Genes Brain Behav, 2:255-67). That experiment provided strong evidence for a specific, and perhaps obligatory, role for coherent gamma oscillation in listening. The decrease in STG gamma oscillation detected from the scalp using MEG in the immediate post-stimulus period therefore suggests a deficit in synaptic integration in ASD that could not only impact listening but also profoundly impact the downstream integration of auditory information in other areas of cortex.

Thus, post-stimulus gamma abnormalities in ASD likely indicate an abnormal excitatory/inhibitory balance in cortical microcircuits, with this imbalance perhaps indicative of an impairment in information processing during passive listening. Deficits in synaptic integration, perhaps due to the loss of fast-spiking interneurons in ASD, may also explain the elevated ASD pre-stimulus activity observed in the present study (Sohal et al. (2009) Nature, 459:698-702). Neural mechanisms other than GABA and inhibitory interneurons, however, influence oscillatory activity, and additional work is needed to determine which factors are of primary importance in ASD. For example, white matter diffusion anisotropy in the acoustic radiations of the auditory pathway is associated with M100 latency (Roberts et al. (2009) Neuroreport., 20:1586-1591) and it is likely that white matter abnormalities in the acoustic radiations also affect signal-to-noise in primary/secondary auditory areas (especially theta to alpha rhythms).

The increase in theta to gamma pre-stimulus activity may be a more general feature of several neurodevelopmental disorders. For example, although increased pre-stimulus gamma has been reported in schizophrenia (Gandal et al. (2012) Neuropharmacol., 62:1504-1518), the individuals with schizophrenia may also show increased prestimulus activity in frequencies below gamma. Finally, it is of interest that only gamma-range activity (pre- and post-stimulus) was related to CELF-4 scores. In the left hemisphere a negative association with CELF-4 scores was observed with early post-stimulus evoked gamma activity (i.e., increased post-stimulus activity associated with lower CELF-4 scores). In the right hemisphere a positive association with CELF-4 scores was observed for the pre-stimulus gamma activity (i.e., increased pre-stimulus activity associated with higher CELF-4 scores). The above suggests that gamma activity is of particular importance in terms of language abilities in ASD.

Notably, the M100 responses were observed less often in the left than in the right hemisphere. For example, for the 500 Hz tone condition, whereas 90% of the children with ASD had an observable right M100 response, only 63% had an observable left M100 response. Data from individuals with ASD with perhaps very abnormal auditory activity (i.e., no identifiable M100 response) were thus not included in the hemisphere-specific time domain and time-frequency analyses. As such, left-hemisphere abnormalities in the present study may be greatly underestimated. Measures of pre-stimulus activity provide support for this claim, as left- but not right-hemisphere pre-stimulus group differences remained after removing variance associated with age.

While the studies used monaural auditory stimuli, binaural auditory stimuli may also be used. The binaural auditory stimuli may allow for a more specific examination of the contributions of ipsilateral versus contralateral pathways to the observed STG auditory abnormalities.

Accordingly, a spectro-temporal profile of ASD was observed herein, such that auditory STG processes in ASD were characterized by pre-stimulus abnormalities, then early high-frequency abnormalities followed by low-frequency abnormalities. Increased pre-stimulus activity appeared as a 'core' abnormality, with pre-stimulus activity predicting post-stimulus neural abnormalities, group membership, and clinical symptoms (CELF-4 Core Language Index). Deficits in synaptic integration in the auditory cortex may be associated with oscillatory abnormalities in ASD as well as patient symptoms. Increased pre-stimulus activity in ASD likely demonstrates a fundamental signal-to-noise deficit in individuals with ASD, with elevations in oscillatory activity suggesting an inability to maintain an appropriate 'neural tone' and an inability to rapidly return to a resting state prior to the next stimulus.

An emerging and promising line of therapies for treating individuals with autism spectrum disorders (ASD) involves manipulation of neurotransmitter release/resorption (especially GABA and glutamate) at the level of the synapse. However, there is little genetic, physiological or behavioral data to identify appropriate candidates for such treatment. Nor is there a methodology for early identification of responders vs. non-responders. Consequently clinical trials are compromised in terms of both inclusion criteria and response measures.

The methodology of the instant invention addresses both of these issues and can thus be considered a family of measures suitable for use as "stratification biomarkers" and "early signals of efficacy." Using magnetoencephalography (MEG) to record brain activity during presentation of simple (or complex) auditory stimuli, one can characterize at least two neural signatures which are atypical in children with ASD. Specifically, these are (i) the latency of the 50 and/or 100 ms response components to auditory stimuli, which are systematically delayed in ASD compared to age-matched controls and (ii) the stimulus elicited activity in the gamma frequency band (~30-50 Hz) which demonstrates diminished inter-trial coherence, ITC, (or "reliability") in children with ASD vs. age-matched typically developing controls. Since these measures characterize the neuronal propagation of signal from sensory input to higher-order processing, they are extremely sensitive to the quality of synaptic transmission, revealing anomalies by virtue of MEG's exquisite temporal resolution (typically <1 ms).

Since novel therapeutics are targeting the synapse in children with ASD, these measures (specifically auditory evoked 50 and 100 ms latencies as well as auditory elicited gamma-band inter-trial coherence (also known as phase locking factor)) represent physiologically-specific indices of (i) an individual's appropriateness for such intervention (stratification biomarker) and (ii) evidence of the desired biological activity of a synaptically-targeted pharmaceutical. This is a necessary precursor of a surrogate marker for clinical outcome.

In accordance with the instant invention, methods of diagnosing a neurological disorder or providing a prognosis of a neurological disorder (particularly an autism spectrum disorder) in a subject are provided. In a particular embodiment, the subject is a child (e.g., up to 18 years of age), particularly a young child (e.g., up to 3, 4, or 5 years of age). In a particular embodiment, the method comprises measuring brain activity using magnetoencephalography after a stimuli, particularly an audio stimuli (e.g., a simple or complex audio stimulus; e.g., an audio signal of about 100 to about 1000 Hz, particularly about 200 to about 700 Hz or about 300 to about 500 Hz). In a particular embodiment, the 50 and/or 100 ms (latency) responses are measured, wherein a delay in the response compared to normal subjects indicates the subject has an autism spectrum disorder. The amount of delay may be correlated to the severity of the autism spectrum disorder. In a particular embodiment, the stimulus elicited activity in the gamma frequency band (about 30 to about 50 Hz, particularly about 40 Hz) is measured, wherein a diminished inter-trial coherence (ITC) compared to normal subjects is indicative of autism spectrum disorder. The severity in decrease may be correlated to the severity of the autism spectrum disorder. In particular embodiment, the subject and controls are age-matched.

In accordance with the instant invention, methods of screening for therapies against a neurological disorder, particularly an autism spectrum disorder, in a subject are provided. In a particular embodiment, the subject is a child (e.g., up to 18 years of age), particularly a young child (e.g., up to 3, 4, or 5 years of age). In a particular embodiment, the method comprises administering a therapy (e.g., administering a compound and/or a non-pharmacological intervention) to the subject and performing the above magnetoencephalography methods, wherein a movement of the results from a baseline of the subject (i.e., before administration of the therapy (e.g., compound)) towards that of a normal subject indicates that the therapy (e.g., compound) is effective against the autism spectrum disorder. The methods may further comprise performing the above magnetoencephalography methods above to establish a baseline prior to the administration of the therapy. Any kind of compound or molecule may be tested as a candidate therapeutic in the methods of the present invention, including, but not limited to, natural or synthetic chemical compounds (such as small molecule compounds), organic and inorganic compounds and molecules, and biological macromolecules (such as saccharide-, lipid-, peptide-, polypeptide- and nucleic acid-based compounds and molecules).

In accordance with another aspect of the instant invention, methods of determining whether a subject is a candidate for a therapy against a neurological disorder, particularly an autism spectrum disorder, are provided. In a particular embodiment, the subject is a child (e.g., up to 18 years of age), particularly a young child (e.g., up to 3, 4, or 5 years of age). In a particular embodiment, the method comprises administering a therapy (e.g., administering a compound and/or a non-pharmacological intervention) to the subject and performing the above magnetoencephalography methods, wherein a movement of the results from a baseline of the subject (i.e., before administration of the therapy (e.g., compound)) towards that of a normal subject indicates that the subject is responsive to the tested therapy (e.g., compound). The methods may further comprise performing the above magnetoencephalography methods above to establish a baseline prior to the administration of the therapy. The therapy may be an approved therapy for the neurological disorder or may be a candidate therapy for the neurological disorder. In a particular embodiment, the instant methods can be used to determine if a patient is appropriate for inclusion in a therapy (e.g., drug) trial. Any kind of compound or molecule may be tested as a candidate therapeutic in the methods of the present invention, including, but not limited to, natural or synthetic chemical compounds (such as small molecule compounds), organic and inorganic compounds and molecules, and biological macromolecules (such as saccharide-, lipid-, peptide-, polypeptide- and nucleic acid-based compounds and molecules).

As demonstrated herein, electrophysiological signatures (e.g., resting activity and evoked responses) serve as biomarkers of neurodevelopmental disorders of neuronal abnormalities in conditions such as autism spectrum disorder (ASD), rendering them detectable very early in development. As autism is typically diagnosed by clinical presentation in young childhood, earlier diagnosis would require sensitivity to atypical brain activity in the young infant (<2-3 years of age). Hence, the magnetoencephalography (MEG) system may be optimized to detect brain activity from children ~6- to ~48-months-old. Accordingly, it is desirable to use an infant and/or child MEG system. An example of a whole-head infant and/or young child MEG system is Artemis123 which is described in Roberts et al. (Frontiers Hum. Neurosci. (2014) 8:1-99).

In addition to the above methods, differences within white matter may also be used in place of or in combination with the electrophysiological auditory responses described in the methods hereinabove. In a particular embodiment, the method comprises using fractional or diffusion anisotropy (e.g., performing diffusion tensor imaging). In a particular embodiment, an increase in axial diffusivity compared to normal subjects indicates the subject has an autism spectrum disorder. In a particular embodiment, a slower rate of maturational decrease of radial diffusivity compared to normal subjects indicates the subject has an autism spectrum disorder.

Definitions

The singular forms "a," "an," and "the" include plural referents unless the context clearly dictates otherwise.

As used herein, the term "subject" refers to an animal, particularly a mammal, particularly a human. As used herein, a "child" refers to a human up to 18 years of age.

The term "autism spectrum disorder" refers to a group of developmental disabilities that includes, without limitation: autism; Asperger syndrome; pervasive developmental disorder not otherwise specified (PDD-NOS or atypical autism); Rett syndrome; and childhood disintegrative disorder. An "autism spectrum disorder" typically refers to a disease or disorder that is characterized by varying degrees of (1) deficits in social interaction, (2) deficits in verbal and nonverbal communication, and (3) repetitive behaviors or interests.

As used herein, "diagnose" refers to detecting and identifying a disease in a subject. The term may also encompass assessing, evaluating, and/or prognosing the disease status (progression, regression, stabilization, response to treatment, etc.) in a patient known to have the disease.

As used herein, the term "prognosis" refers to providing information regarding the impact of the presence of a disease on a subject's future health (e.g., expected morbidity or mortality, the likelihood of developing disease, and the severity of the disease). In other words, the term "prognosis" refers to providing a prediction of the probable course and outcome of the disease or the likelihood of recovery from the disease.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The following examples are provided to illustrate various embodiments of the present invention. They are not intended to limit the invention in any way.

EXAMPLE 1

Methods
Participants

Recruitment procedures and inclusion/exclusion information are detailed in Roberts et al. (Autism Res. (2010) 3:8-18). Although individuals with ASD were not screened for comorbid disorders (e.g., ADHD), individuals with known neurological or genetic conditions (e.g., seizure disorder, head injury, Fragile X) or mental retardation (Nonverbal and Verbal IQ both below 75) were excluded. Data were analyzed from 105 children with ASD (11 Female) and 36 TD (19 females) children. In the children with ASD, mean score on the Autism Diagnostic Observation Schedule was 12.5 (SD=4.44; module 3 administered in nearly all cases), mean score on the Social Responsiveness Scale was 81.73 (SD=20.27), and mean score on the Social Communication Questionnaire was 20.77 (SD=9.49).

The age range of both groups was 6 to 16 yrs, and t-tests demonstrated that the groups were similar in age (TD=10.90 yrs+/−2.78; ASD=10.07 yrs+/−2.37; t(139)=1.74, ns). Groups did not differ on their Wechsler Intelligence Scale for Children-IV Perceptual Reasoning Index scores (TD=108.83+/−14.64; ASD=103.61+/−15.18; t(139)=1.80, ns). Individuals with ASD had lower CELF-4 Core Language Index scores (TD=109.44+/−11.29; ASD=88.70+/−19.37; t(139)=6.08, p<0.01).

Auditory Stimuli

Auditory stimuli were delivered via eartip inserts (Etymotic ER3A, Elk Grove, Ill.). Children with ASD tended to have weaker hearing (detection thresholds ~5 dB higher than the TD group), and the TD and ASD groups differed in hearing thresholds in the left, t(137)=1.94, p<0.05, and right ear, t(118)=2.88, p<0.01 (two participants were missing threshold information). Stimuli, however, were presented 45 dB above individually-determined thresholds, controlling for individual (and group) hearing threshold differences. During the MEG exam, 200, 300, 500 and 1000 Hz sinusoidal tones of 300 ms duration (with 10 ms onset-offset ramps) were presented binaurally. Tones were randomly presented, with a 1 s interstimulus interval (jittered +/−100 ms). Over approximately 7 min of recording time, 105 tones at each of the 4 frequencies were presented.

MEG Recordings

Recordings were obtained using a 275-channel MEG system (VSM MedTech Inc., Coquitlam, BC). Three head-position indicator coils attached to the scalp provided continuous specification of the position and orientation of the MEG sensors relative to the head. To minimize fatigue, subjects viewed (but did not listen to) a movie projected onto a screen positioned at a comfortable viewing distance. To aid in the identification of eye-blink activity, the electro-oculogram (EOG; bipolar oblique, upper right and lower left sites) was collected. Electrodes were also attached above the left and right collar bone for electrocardiogram (ECG) recording. After a bandpass filter (0.03-300 Hz), EOG, ECG, and MEG signals were digitized at 1200 Hz, with 3rd order gradiometer environmental noise reduction for the MEG data.

MEG Data Analysis

Epochs (500 ms pre-stimulus to 500 ms post-stimulus) were defined from the continuous recording. Eye-blink and heartbeat activity were corrected using procedures outlined in Roberts et al. (Autism Res. (2010) 3:8-18). Epochs with artifacts other than blinks or heartbeat were rejected by amplitude and gradient criteria (amplitude>1200 fT/cm, gradients>800 fT/cm/sample). Noncontaminated epochs were averaged according to stimulus type.

Determination of the strength and latency of M100 sources in the left and right STG was accomplished by applying a standard source model to transform each individual's raw MEG surface activity into brain space (MEG data co-registered to the Montreal Neurologic Institute (MNI) averaged brain) using a model with multiple sources (Scherg, M. (1990) Fundamentals of dipole source potential analysis, in Auditory evoked magnetic fields and electric potentials. Advances in audiology, M. H. G. L. R. Gandori, Editor. Karger: Basel, Switzerland. p. 40-69; Scherg et al. (1996) Electroencephalogr Clin Neurophysiol Suppl., 46:127-37; Scherg et al. (1985) Electroencephalogr Clin Neurophysiol, 62:290-9). The source model was constructed by including (1) left and right STG dipole sources, and (2) nine fixed regional sources that model brain background activity and serve as probe sources for additional oscillatory activity. The eye-blink source vector derived for each participant was also included to remove eye-blink activity (Berg et al. (1994) Electroencephalogr Clin Neurophysiol, 90:229-41; Lins et al. (1993) Brain Topogr, 6:65-78). The final source model serves as a source montage for the raw MEG (Scherg et al. (1994) Neurophysiol Clin, 24:51-60; Scherg et al. (2002) J Clin Neurophysiol, 19:91-112). Although the strength and latency of the M100 STG responses were obtained using a dipole source placed at a standard location, in each subject left and right hemisphere dipoles were oriented at the maximum of the M100. As such, although position was fixed, orientation of the standard STG sources was optimized for each subject.

To measure M100 STG latency, a 1 Hz (6 dB/octave, forward) to 40 Hz (48 dB/octave, zero-phase) bandpass filter was applied and left and right M100 STG peak latency (measured in nano-Ampere-meters, nAm) was calculated from the largest point in the M100 scoring window (90 to 190 ms) using in-house MatLab software.

The calculation of single-trial phase and magnitude for the left and right STG sources used a modification of procedures (Hoechstetter et al. (2004) Brain Topogr, 16:233-8.) where in each participant the derived source model was applied to the raw unfiltered data. Transformation from the time domain to the time-frequency domain used complex demodulation procedures (Papp et al. (1977) Biomed Sci Instrum, 13:135-45) implemented in BESA 5.2, using frequencies between 4 and 80 Hz, in steps of 2 Hz.1 Continuous data were analyzed relative to the tone onset every 25 ms, utilizing +/−39.4 ms and +/−2.83 Hz (full width at half maximum parameters) of contiguous data at each 25 ms step. Time-frequency measures were computed from −400 to 400 ms relative to stimulus onset. For evoked activity, background activity at each frequency (average power −400 to −100 ms) was calculated and subtracted as a function of frequency. In addition to evoked activity, for each time-frequency bin, a measure of phase-locking referred to as inter-trial coherence was computed as $$\text{abs}\left(\frac{1}{N}\sum_{k=1}^{N}e^{i\phi(k)}\right),$$

where the sum is over all N trials, and Ø (k) is the phase of the signal in the $k^{th}$ trial. Inter-trial coherence (ITC) is a normalized measure with ITC=1 reflecting no phase variability and ITC=0 reflecting maximal phase variability across trials (Lachaux et al. (1999) Hum. Brain Mapp, 8:194-208).

Group Comparisons

For the time-domain analyses, unpaired t-tests probed group differences in M100 source strength and latency. Primary time-frequency analyses used t-tests to examine activity at each even-number frequency between 4 to 80 Hz in 25 ms bins and from 0 to 400 ms following stimulus onset, resulting in 624 t-tests (39 frequencies×16 time bins) for each hemisphere. To control family-wise error, a clustering method (which computes the probability of a random field of noise producing a cluster of a given size after the noise is thresholded at a given probability level) was used to obtain a corrected p-value. The cluster size needed to obtain the desired familywise correction was determined using a standard fMRI package (AFNI AlphaSim, B. Douglas Ward), and clustering was performed with custom MatLab software. Using time (x axis) and frequency (y axis) full width at half maximum parameters that characterized the time-frequency filters (i.e., time=+/−39.4 ms and frequency=+/− 2.83 Hz), an initial p-value threshold of 0.05 for each time-frequency value and a cluster size threshold of 12 values (adjacent in time and/or frequency) provided a family-wise corrected p=0.05.

Given differences in the percentage of males and females in each group, time-frequency analyses were re-run removing females (there were not enough females in the ASD group to compute female-only analyses). In addition, given the large age range (6 to 16 yrs), where time-frequency group differences were observed, region-of-interest analyses were run with age as a covariate to determine if the group differences remained after controlling for age (given that groups did not differ on age, the use of age as a covariate was appropriate).

Finally, associations between each of the time-frequency measures and symptom severity were examined using the CELF-4 Core Language Index and the General Ability Index (GAI) IQ measure obtained from the Wechsler Intelligence Scale for Children-IV (WISC-IV; Wechsler, D., Wechsler Intelligence Scale for Children 3rd ed. 2003, San Antonio, Tex.: The Psychological Corporation). The GAI provides an index of IQ without the confound of working memory and processing speed. Finally, correlations were also used to examine associations with age. As with the group comparisons, random field clustering controlled family-wise error in all correlation analyses.

Results

STG Latency

M100.

Group latency differences were observed only in the right hemisphere. The right-hemisphere M100 response peaked later in ASD than TD at 300 Hz (t(119)=1.57, p=0.12; marginally significant) and 500 Hz (t(127)=2.49, p=0.01), with an 7 ms and ~10 ms delay in the children with ASD for right hemisphere response to 300 Hz and 500 Hz tone stimuli, respectively.

STG Time-Frequency Activity

Evoked Oscillatory Activity.

As shown in FIG. 1, corrected clusters indicated a smaller increase in gamma evoked activity from ~50 to ~150 ms in the ASD than TD group (blue clusters). Gamma group differences were observed bilaterally and for all stimuli, although most prominent for 200, 300 and 500 Hz stimuli. Low-frequency evoked group differences were observed only in the right hemisphere at 500 Hz, the hemisphere and stimulus frequency where M100 group latency differences were most prominent.

Evoked time-frequency analyses were re-run including only males. Except for right 500 Hz where gamma group differences were marginally significant, the pattern of findings was unchanged. Examining ROIs where group differences were observed and re-running analyses with age as a covariate (full sample), the pattern of findings was unchanged.

Inter-Trial Coherence (ITC).

As shown in FIG. 2, corrected clusters indicated decreased left- and right-hemisphere gamma ITC in the ASD versus the TD group from ~50 to ~200 ms (clusters) at 300, 500, and 1000 Hz (although the grand average plots suggest right gamma group differences at 200 Hz, this did not reach significance in this sample). ITC measures were more sensitive to low-frequency group differences than evoked measures. In particular, decreased low-frequency ITC in the ASD than TD group was observed from 50 ms onwards at all frequencies except 1000 Hz.

ITC time-frequency analyses were re-run including only males. The pattern of findings was unchanged for left 300 Hz and marginally significant for right 300 Hz. Excluding males, no group differences were resolved for left or right 500 Hz gamma activity. Examining ROIs where group differences were observed and re-running analyses with age as a covariate (full sample), the pattern of findings was unchanged.

Pre-Stimulus Oscillatory Activity.

Given that the four tones (i.e., 200, 300, 500, and 1000 Hz) were randomly presented, group pre-stimulus differences were assessed after averaging the trials for all tones (approximately 420 trials). The pre-stimulus measure was computed by time-frequency transforming each trial and then averaging (i.e., a pre-stimulus total power measure was computed). Table 1 shows that except for right STG high gamma, group differences were observed at all examined frequencies (i.e., theta, alpha, beta, low gamma, high gamma), with pre-stimulus power elevated in ASD.

TABLE 1

Pre-stimulus group differences were assessed after averaging the trials for all tones (approximately 420 trials). Group means (SD) and p-values are reported for the left and right STG for theta, alpha, beta, low gamma, and high gamma.

| Frequency band | TD left STG | ASD left STG | p value | TD right STG | ASD right STG | p value |
|---|---|---|---|---|---|---|
| Theta (4-8 Hz) | 45.84 (13.39) | 55.52 (17.16) | p = 0.003 | 41.52 (10.14) | 49.46 (13.45) | p = 0.002 |
| Alpha (8-12 Hz) | 30.38 (9.31) | 35.47 (11.50) | p = 0.02 | 27.17 (6.75) | 31.41 (9.093) | p = 0.01 |

TABLE 1-continued

Pre-stimulus group differences were assessed after averaging the trials for all tones (approximately 420 trials). Group means (SD) and p-values are reported for the left and right STG for theta, alpha, beta, low gamma, and high gamma.

| Frequency band | TD left STG | ASD left STG | p value | TD right STG | ASD right STG | p value |
| --- | --- | --- | --- | --- | --- | --- |
| Beta (13-20 Hz) | 19.12 (5.00) | 22.94 (6.91) | p = 0.003 | 18.07 (4.38) | 20.72 (5.44) | p = 0.01 |
| Low Gamma (20-56) | 7.84 (1.58) | 9.52 (2.39) | p < 0.001 | 8.06 (1.70) | 9.07 (2.33) | p = 0.02 |
| High Gamma (64-80 Hz) | 4.80 (1.17) | 6.13 (1.76) | p < 0.001 | 5.80 (1.85) | 6.13 (2.11) | p = 0.42 |

Examining only males, the pattern of findings was unchanged for all pre-stimulus group comparisons. Re-running the analyses with age as a covariate (full sample), except for the right low and high gamma group comparisons becoming non-significant after removing variance associated with age, the pattern of findings was unchanged for all other pre-stimulus group comparisons.

Predicting Right M100 STG Latency

To determine if time-frequency measures predicted right-hemisphere M100 STG latency and thus might account for the ASD latency delay, correlations indexed associations between M100 latency and pre-stimulus activity as well as post-stimulus activity preceding the M100 response. Greater left and right STG pre-stimulus activity (4 to 80 Hz) was associated with a longer M100 latency, with focused analyses showing that this association was generally observed across all frequency bands in both hemispheres. No post-stimulus time-frequency measure prior to M100 was associated with right M100 latency. As such, the functional significance of pre-stimulus electrophysiological anomaly is implicated.

To further examine associations between pre-stimulus activity, Group, and M100 latency, a hierarchical regression was performed with 4 to 80 Hz pre-stimulus activity entered first (given pre-stimulus group differences at most frequencies a single measure was computed), group second, and their interaction last, with M100 latency as the dependent variable. Regressions were conducted only where group latency differences were observed: right hemisphere response to 500 Hz tones. Added first, pre-stimulus activity accounted for significant variance (r2=0.07, p<0.01). Added second, Group account for significant additional variance (r2=0.02, p<0.05), indicating that both pre-stimulus activity and Group predicted unique variance in M100 latency. The interaction term was not significant.

Associations with Clinical Measures

Figure 3:
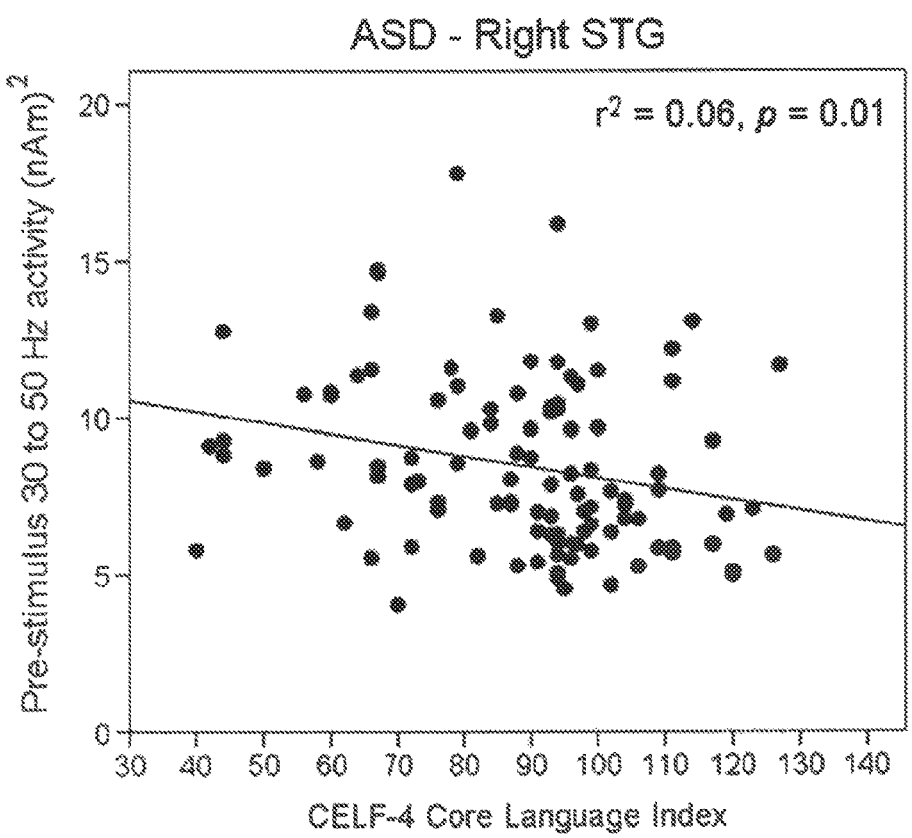

Correlations indexed associations between time-frequency (i.e., evoked, ITC, and pre-stimulus activity) and CELF-4 Core Language Index and GAI scores in ASD. Examining the family-wise corrected correlation maps, only associations with gamma activity were observed. In the left hemisphere, lower CELF-4 Core Language Index scores were associated with increased early 100 Hz post-stimulus evoked gamma (r=0.33, p<0.001; similar relationships not observed for any other frequency in either hemisphere). As shown in FIG. 3, there was a relationship between poorer performance on the CELF-4 Core Language Index and increased 30 to 50 Hz right-hemisphere pre-stimulus activity (r=0.36, p=0.01). No associations with GAI scores were observed.

Associations with Age

Figure 4:
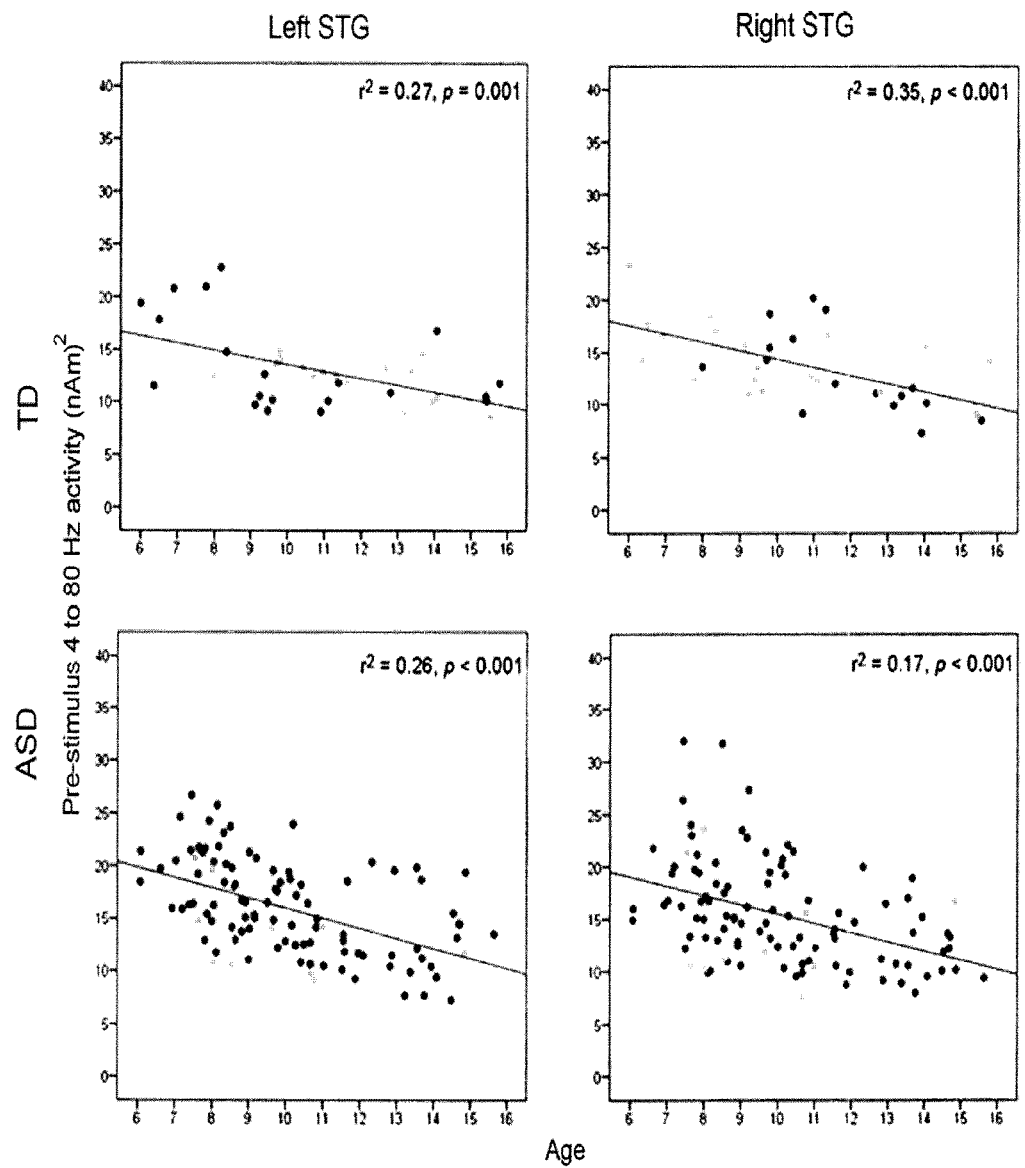
FIG. 4 provides scatterplots of age (x axis) and pre-stimulus total power (average of 4 to 80 Hz activity). In TD (top row) and ASD (bottom row), increased pre-stimulus activity predicted a younger age. Males are shown in blue and females in pink.

A relationship between age and M100 latency has been observed. In the present study, zero-order correlations showed that age predicted M100 latency for all tones (rs>0.40, ps<0.003). As shown in FIG. 4, a strong association between age and pre-stimulus activity (average across tones) also was observed.

To examine the extent to which age accounts for M100 latency and pre-stimulus group differences, hierarchical regressions were performed with Age entered first, Group second, and their interaction last, with M100 STG latency or right STG pre-stimulus activity (4 to 80 Hz) as the dependent variable. With M100 latency as the dependent variable, the full regression model (Age, Group, interaction) accounted for significant variance in M100 latency (ps<0.01). For all analyses (i.e., each hemisphere and each tone), added first, Age accounted for significant variance (ps<0.001). Neither the Group nor the interaction term accounted for additional variance (Group marginally significant for right-hemisphere response to 500 Hz stimulus, p=0.08).

With the pre-stimulus activity as the dependent variable, the full regression model (Age, Group, interaction) accounted for significant variance in pre-stimulus activity (ps<0.001). Added first, Age accounted for significant variance (left hemisphere=28%, p<0.001; right hemisphere=22%, p<0.001). Group accounted for additional variance only in the left hemisphere (5%, p<0.003). The interaction terms were not significant.

EXAMPLE 2

Figure 5:
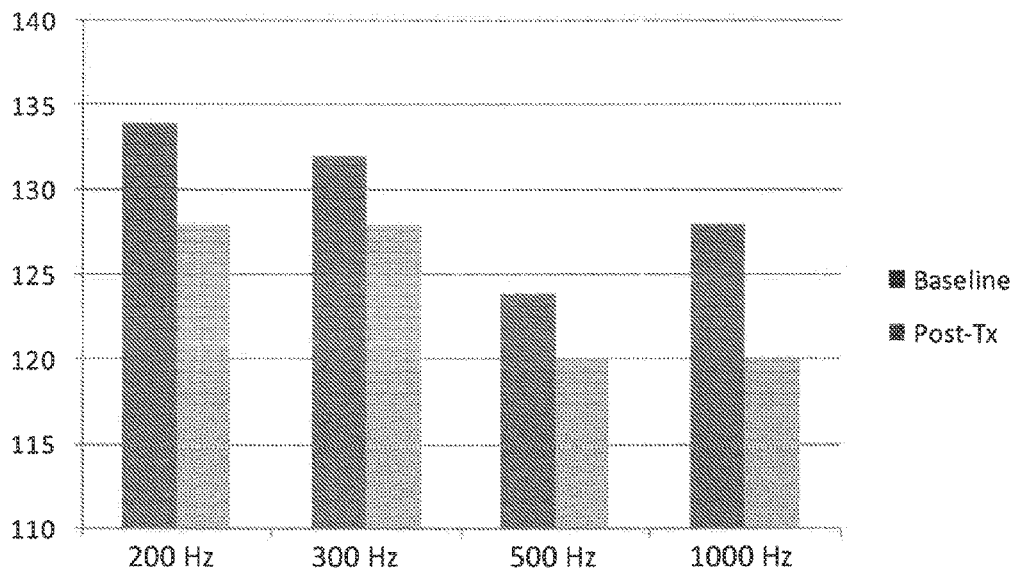
FIG. 5 provides graphs of M100 latency in autism in response to STX209, showing baseline and post-treatment.
Figure 5:
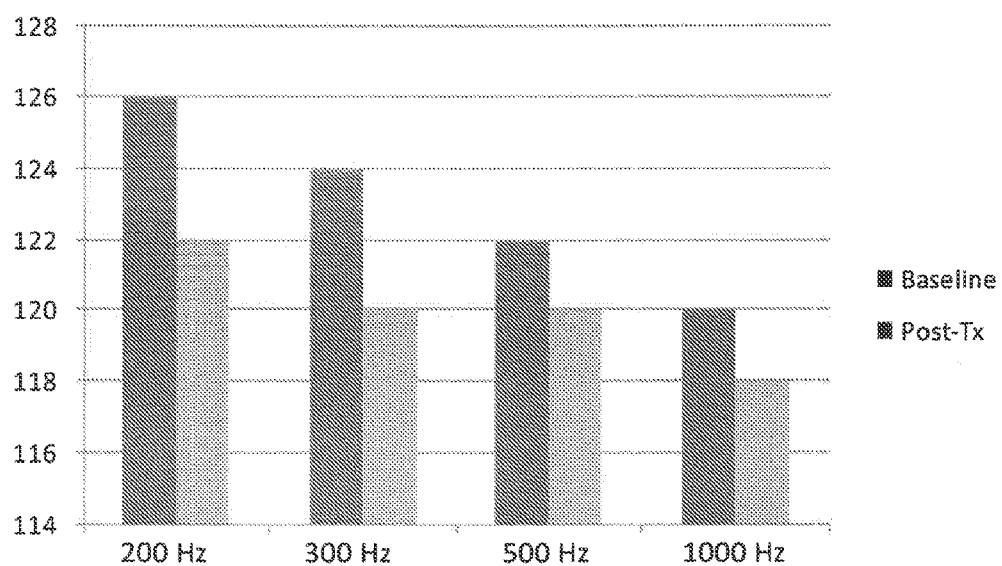
Figure 6:
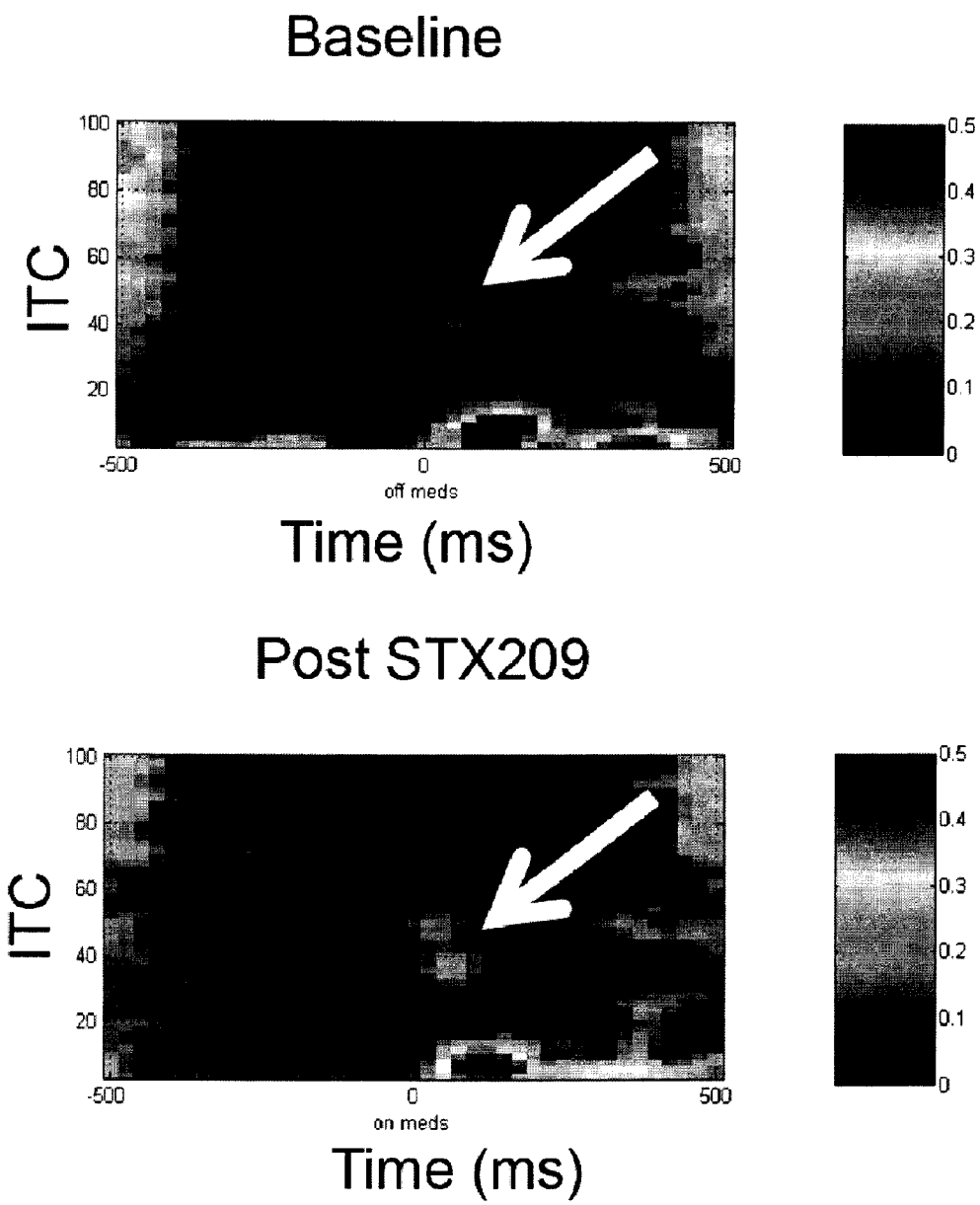
FIG. 6 shows the MEG measures of inter trial coherence in autism response to STX209.
Figure 7:
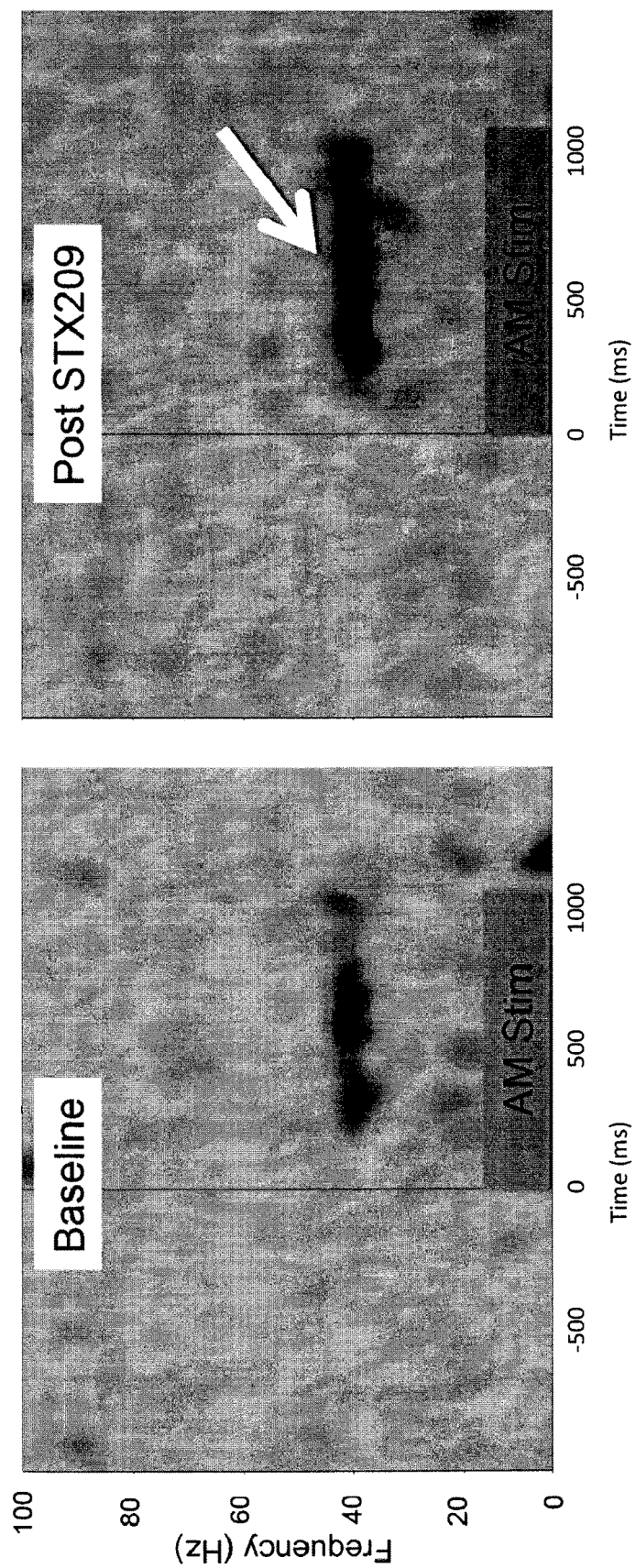
FIG. 7 shows the MEG measures of steady state gamma in autism in response to STX209.

A single subject from a recent phase/T clinical trial of STX209 (arbaclofen), a GABA-8 agonist, underwent MEG at baseline and at 12 weeks after treatment. FIG. 5 shows that the auditory M100 latency is shortened post-treatment. Indeed, a reduction in 100 ms latency for 4 stimuli in both hemispheres was observed. FIGS. 6 and 7 demonstrate an elevation of gamma-band inter-trial coherence in both hemispheres. FIG. 6 shows that no significant gamma ITC existed at baseline whereas gamma band ITC was restored after treatment. FIG. 7 shows that steady state gamma power (elicited by AM tone, driven at 40 Hz) is boosted post-treatment.

EXAMPLE 3

During typical development, myelination of white matter (WM) confers electrical insulation to allow more efficient axonal signal conduction. This myelination is a critical determinant in processing basic sensory information as well as increasing processing speed during more complex cognitive tasks (Dockstader et al. (2012) Hum. Brain Mapp. 33,179-191; Kandel et al. (1991) In: Principles of Neural Science. Elsevier Science Publishing Co., Inc., New York; Stufflebeam et al. (2008) NeuroImage 42:710-716). Due to the importance of myelination during development, an investigation of white matter maturation and its consequences in individuals with developmental disorders is of interest. Diffusion tensor imaging (DTI) allows indirect measurement of white matter maturation and of the microstructural properties of WM through fractional anisotropy (FA), a measure of the organization of water diffusion (Beaulieu, C. (2002) NMR Biomed., 15:435-455; Harsan et al. (2006) J. Neurosci. Res. 83:392-402).

Whereas DTI provides measures of brain structure, magnetoencephalography (MEG) permits recording of neural activity with high temporal resolution. Thus MEG's functional complement to DTI's microstructural data offers insight into the relationship between brain anatomy and function (Dockstader et al. (2012) Hum. Brain Mapp. 33,179-191; Roberts et al. (2009) Neuro Report 20:1586-1591; Roberts et al. (2010) Autism Res., 3:8-18; Stufflebeam et al. (2008) NeuroImage 42:710-716). DTI studies have found an increase in FA with age throughout childhood (Ashtari et al. (2007) NeuroImage 35:501-510; Hasan et al. (2007) NeuroImage 34:1497-1505.; Schmithorst et al. (2002) Radiology 222:212-218), and other studies have shown an inverse relationship between age and the latency of evoked responses in children (Paetau et al. (1995) J. Clin. Neurophysiol., 12:177-185; Roberts et al. (2009) Neuro Report 20:1586-1591; Roberts et al. (2010) Autism Res., 3:8-18). The maturational relationship of FA and latency with development has prompted examination of an association between these measures (Dockstader et al. (2012) Hum. Brain Mapp. 33,179-191; Roberts et al. (2009) Neuro Report 20:1586-1591; Stufflebeam et al. (2008) NeuroImage 42:710-716), with studies indicating a link between increasing FA and decreasing latency as a biophysical feature of developmental change (Roberts et al. (2009) Neuro Report 20:1586-1591).

Atypical white matter FA and delayed auditory responses in children with ASD versus typically developing (TD) children has been demonstrated (Lange et al. (2010) Autism Res., 3:350-358; Lee et al. (2007) Neurosci. Lett., 424:127-132; Gage et al. (2003) NeuroReport 14:2047-2051; Gage et al. (2003) Brain Res. Dev. Brain Res., 144:201-209; Oram Cardy et al. (2008) Int. J. Psychophysiol., 68:170-175; Roberts et al. (2008) Int. J. Psychophysiol., 68:149-160; Roberts et al. (2010) Autism Res., 3:8-18). Furthermore, an associations between FA of the acoustic radiations (a critical WM pathway extending from the medial geniculate nucleus of the thalamus to the primary auditory cortex in the superior temporal lobe) and the latency of the 100 ms auditory response (M100) in TD children has been observed, with both FA and M100 latency showing age-dependent developmental changes (Roberts et al. (2009) NeuroReport 20:1586-1591).

The present study examines the earlier "middle latency" cortical 50 ms auditory response (M50) and M50 latency associations with age and FA of the thalamocortical projections (Reite et al. (1988) Electroencephalogr. Clin. Neurophysiol., 70:490-498). Some (N=24) of the TD individuals reported by Roberts et al. (2009) NeuroReport 20:1586-1591 are included in the present cohort (although the MEG paradigm and auditory response of interest differ between the studies). It was hypothesized that group differences would be observed in the rate of maturation of the M50 latency and WM thalamocortical projections, as well as group differences in associations between these measures, with the ASD population demonstrating a weaker relationship between M50 latency and FA.

Experimental Procedures

Participants were 41 TD children/adolescents (mean age=10.88, SD=2.70) and 58 children/adolescents with ASD (age=10.41, SD=2.51). Groups did not differ in age ($p=0.37$). ASD diagnosis was previously made based on expert clinician judgment of DSM-IV criteria and confirmed during study participation by empirically established cut-offs on the Autism Diagnostic Observation Schedule (ADOS) as well as parent-completed questionnaires, including the Social Communication Questionnaire (SCQ) and the Social Responsiveness Scale (SRS) (for additional details on subject recruitment as well as exclusion and inclusion criteria see Roberts et al. (2010) Autism Res., 3:8-18). Scores on Clinical Evaluation of Language Fundamentals (CELF-4) Core Language Index and Wechsler Intelligence Scale for Children (WISC-IV) Full Scale IQ, Perceptual Reasoning Index (PRI), and Verbal Comprehension Index (VCI) were also obtained.

Structural Measures

DTI consisted of whole-brain 2×2×2 mm$^3$ isotropic acquisitions in the axial plane with 30 directions and b-value of 1000 s/mm$^2$ at 3T (Siemens Verio™, Siemens Medical Solutions, Erlangen, Germany) using a modified monopolar Stejskal-Tanner sequence with TE of 70 ms, TR of 11 s, spin-echo echoplanar sequence, a 32-channel head coil, maximal gradient strength of 45 mT/m, and a parallel acquisition factor of 2 with generalized autocalibrating partially parallel acquisition. Post-processing involved calculation of tensor eigenvalues, FA, and fiber tracking. Analyses were performed in DTIStudio using the Fiber Assignment by Continuous Tracking (FACT) algorithm with an FA threshold of 0.25 and an angle cutoff of 70° (Mori et al. (1999) Ann. Neurol., 45:265-269; Paetau et al. (1995) J. Clin. Neurophysiol., 12:177-185). Image quality of each case was visually inspected for any indication of artifact due to metal and/or motion. Cases where such artifact was observed were excluded from analysis (Roberts et al. (2010) Autism Res., 3:8-18).

DTI analyses examined left and right acoustic radiations, the thalamocortical projections connecting the medial geniculate nucleus to the primary auditory cortex of the superior temporal lobe. Regions of interest (ROIs) were drawn on axial directionally color-coded FA maps and interrogated directly for FA. Fiber tracking by placing seeds within the left and right ROIs also allowed reconstruction of the fiber tracts of the left and right acoustic radiations and was used to confirm ROI placement. To further explore details of the microstructure of the thalamocortical pathways, mean diffusivity (MD), axial diffusivity (AD) and radial diffusivity (RD) measures were also computed. These parameters are related by the three eigenvalues of the diffusion tensor:axial diffusivity is equal to the value of the principal eigenvalue ($\lambda_1$) and radial diffusivity is the arithmetic mean of the second and third eigenvalues (($\lambda_2+\lambda_3$)/2). Mean diffusivity is computed as the arithmetic mean of all three eigenvalues (and can thus be considered as a 2:1 weighted average of RD and AD). FA can be considered as the standard deviation of the three eigenvalues.

Functional Measures

Prior to data acquisition, 1000 Hz tones of 300 ms duration and 10 ms rise time were presented binaurally and incrementally until reaching auditory threshold for each ear. Tones during the task were presented at 45 dB sensation level (above threshold). Task stimuli consisted of 1000 Hz and 2000 Hz tones presented using Eprime v1.1. Tones were presented via a sound pressure transducer and sound conduction tubing to the subject's peripheral auditory canal via ear-tip inserts (ER3A, Etymotic Research, Illinois). Each stimulus trial consisted of a 50 ms tone (randomly presented 1000 Hz and 2000 Hz tones) and a 2350 ms (±100 ms) inter-trial interval. Artifact-contaminated epochs were rejected, non-artifact epochs averaged, and a 1 Hz (6 dB/octave, forward) to 40 Hz (48 dB/octave, zero-phase) bandpass filter applied.

MEG analyses focused on the latency of the M50 response. Applying methods outlined by Roberts et al. (2009) NeuroReport 20:1586-1591, using all 275 channels of MEG data, determination of the peak latency of M50 sources was accomplished by applying to each participant a standard source model that included left and right STG sources in order to transform each participant's raw MEG surface activity into brain space (Scherg et al. (1985) Electroencephalogr. Clin. Neurophysiol. 62:32-44). Bilateral STG sources were oriented for each subject at M50 peak amplitude. M50 peaks were picked using methods similar to those described by Roberts et al. (2009) NeuroReport 20:1586-1591, with the M50 peak being the first peak with appropriate sensor-level topography immediately preceding M100 and in a scoring window of 30-130 ms post-stimulus on set. M50 latency responses were scored using in-house MATLAB software correcting for baseline. The extended latency range of the M50 scoring window accommodated the longer M50 latencies observed in young children and ASD (Roberts et al. (2010) Autism Res. 3:8-18).

Repeated-measure ANOVA assessed main effects of group and hemisphere as well as group×hemisphere interactions. Since hemisphere effects were not significant for acoustic radiation FA, further analyses were conducted collapsing across hemisphere. Group differences in marginal mean FA and M50 latency were assessed with an age-covaried general linear model. Group differences in the association between FA and M50 latency with age were examined using hierarchical linear regression with age entered first, group second, and the interaction term (i.e., group×M50 latency) third. Group differences in associations between FA and M50 were similarly examined using hierarchical linear regression.

Results

Seven subjects were excluded from final analyses because they were unable to complete the MRI exam (2 ASD) or because of excessive metal artifact in the MEG data (2 TD, 3 ASD). Useable data was obtained from 39 TD children/adolescents (mean age=11.02, SD=2.68) and 53 children/adolescents with ASD (age=10.42, SD=2.43). In this slightly reduced sample, groups did not differ in age ($p=0.23$).

Repeated-measure ANOVA indicated no main effect of hemisphere for FA ($F=1.34$, $p=0.24$), with no significant group or group×hemisphere interactions. As such, subsequent analyses collapsed across hemisphere, averaging left and right DTI or MEG. For M50, in cases where bilateral responses were not observed (no left M50 in 8 subjects (3 TD and 5 ASD) and no right M50 in 15 subjects (4 TD and 11 ASD)), only the discernible response was used. No group or hemispheric difference in the presence of M50 was observed (Fisher Exact Test, $p>0.05$). In addition, subjects with or without an M50 response did not differ in age or FA. For further analyses, hierarchical regressions examining FA and M50 latency were performed, entering age first, diagnosis second, and the interaction term third.

For age-corrected marginal mean FA, there was no difference between the TD (mean 0.37±0.049) and ASD (mean 0.36±0.047) groups, $F=0.07$, $p=0.79$. For age-corrected marginal mean M50 latency, there was a significant difference between the TD (mean 67.67±14.94) and ASD (mean 73.49±14.27) groups, $F=4.31$, $p=0.04$, with a latency prolongation (~10%) in ASD consistent with the M100 latency findings.

M50 latency decreased with age in TD ($r=0.43$, $p<0.01$, slope=$-2.4$ ms/yr) and ASD ($r=0.44$, $p<0.01$, slope=$-2.6$ ms/yr). The group difference between slopes was not significant ($p=0.43$).

FA increased with age in TD ($r=0.50$, $p<0.01$, slope=0.009/yr) but not in ASD ($r=0.11$, $p=0.44$, slope=0.002/yr). The group difference between slopes was significant ($p=0.03$).

M50 latency decreased with increasing FA in TD ($r=0.42$, $p<0.01$, slope=$-127.13$) but not in ASD ($r=0.028$, $p=0.85$, slope=8.37). The group difference between slopes was significant ($p=0.03$).

Considering the TD group only, after regressing out effects of age on FA ($p<0.01$), a residual association with CELF-4 CLI was significant ($p=0.054$), with a positive slope of 0.001 FA units per point increase in CELF-4 CLI. This positive association was apparently lost in the ASD group (reminiscent of the loss of FA versus M50 relationship), with ASD CELF-4 accounting for only 1% $R^2$ change in FA ($p=0.46$). In neither ASD nor TD was an association with non-verbal IQ (PRI of the WISC-IV) identified ($p>0.05$). For M50 latency, similar to the M100 findings in SLI, no association was found with CELF-4 CLI for TD or ASD ($p>0.05$).

The results also showed a lack of main effects of hemisphere. Collapsing M50 latency values across hemispheres revealed a statistically significant ($p<0.05$) delay in M50 latency in ASD compared to that in TD. There were no between group differences in marginal mean FA, for either hemisphere, or for values collapsed across hemispheres. M50 latency decreased with age in TD in the left hemisphere ($r=0.34$, $p<0.05$, slope=$-2.2$ ms/yr) and right hemisphere ($r=0.53$, $p<0.05$, slope=$-2.8$ ms/yr). There was no significant within-group difference between hemispheres ($p=0.63$). M50 latency decreased with age in ASD in the left hemisphere ($r=0.45$, $p<0.05$, slope=$-2.9$ ms/yr) and the right hemisphere ($r=0.25$, $p=0.11$, slope=$-1.6$ ms/yr). The group difference between slopes was not significant for either hemisphere ($p>0.36$). Collapsed across hemispheres there was a significant age-dependent shortening of M50 latency in both groups, that did not differ significantly in slope, although a significant difference in intercept reveals persistent M50 latency delay in ASD compared to that in TD. FA increased with age in TD in the left hemisphere ($r=0.33$, $p<0.05$, slope=0.007/yr) and right hemisphere ($r=0.50$, $p<0.05$, slope=0.011/yr). FA did not change with age in ASD in the left hemisphere ($r=0.08$, $p=0.55$, slope=0.002/yr) or right hemisphere ($r=0.09$, $p=0.54$, slope=0.002/yr). The group difference between slopes was not significant for the left ($p=0.19$) but was significant for the right hemisphere ($p<0.05$). Collapsing across hemisphere revealed significant group differences in the slope (TD=0.002 units/yr; ASD=0.009 units/yr, $p<0.05$). M50 latency decreased with increasing FA in TD in the left ($r=0$, $p<0.05$, slope=$-102.16$) and right hemisphere ($r=0$, $p<0.05$, slope=$-87.19$). M50 latency did not change with FA in ASD in the left ($r=0$, $p=0.24$, slope=44.22) or the right hemisphere ($r=0$, $p=0.39$, slope=$-40.46$). The group difference between slopes was significant in the left ($p<0.05$) but not in the right hemisphere ($p=0.44$).

To understand the biological underpinning of the reduced age-dependence of fractional anisotropy (FA) in ASD versus TD, the related diffusion parameters mean, axial and radial diffusivity (MD, AD, RD) were analyzed. Individuals with ASD had increased axial diffusivity versus TD ($p<0.05$). Individuals with ASD showed a maturational decrease of radial diffusivity but at a slower rate than that observed in TD. Also, individuals with ASD showed a non-significant tendency towards an axial diffusivity decrease with age, whereas the TD group showed a lack of age-dependence on axial diffusivity.

As hypothesized, FA of the acoustic radiations was positively associated with age (although only in TD children), and M50 latency was negatively associated with age (for both TD and ASD). Examining between-group differences, the ASD group showed a delayed M50 response. Of interest, although the ASD group had a delayed M50 response, the slope of the M50 latency versus age relationship did not differ between groups; rather, the intercept did. In addition, although there was no group difference in mean acoustic radiation FA between groups (correcting for age), FA increased with age in the TD but not in the ASD group. In fact, a major finding of this study is the apparent absence, or at least considerable slowing, of developmental change in the acoustic radiation FA in children with ASD.

In the TD group, FA of the acoustic radiations was related to age and M50 latency, suggesting a role of WM development in the maturation of the auditory cortex electrophysiologic response. In the ASD group, although M50 latency showed a significant maturational age dependence, it was not significantly associated with acoustic radiation FA, indicating an uncoupling between the structure-function relationship of auditory cortex electrophysiology and thalamocortical white matter in ASD. Thus factors other than white matter conduction velocity impact the maturation of the auditory evoked response and at least some of these factors do not exhibit an atypical developmental rate in ASD. Studies of these factors, such as synaptic transmission, are of interest. As an example, Edgar et al. (2013) showed that pre-stimulus power predicts M100 response latencies, with increased pre-stimulus power (i.e., more noise) predicting longer M100 response latencies.

In contrast to FA, mean diffusivity of the acoustic radiations decreased with age in ASD in a similar fashion to TD. However, examination of underlying axial and radial diffusivity changes suggests that the mechanisms underlying the mean diffusivity finding differ between groups. In particular, radial diffusivity tended to decrease at a slower rate in ASD than in TD, whereas axial diffusivity tended to decrease in ASD while being asymptotic in TD. The combination of these trends accounts for the significant difference in age-slopes between ASD and TD observed for FA, and the lack of group difference in age-slopes of MD. Considering the M50 developmental trajectory in ASD, which did not differ in slope from that observed in TD, a shift of 5-6 ms persisted in the ASD compared to the TD group at each age, perhaps attributable to the atypical WM maturation in the ASD group. Despite the age-related changes in axial diffusivity and radial diffusivity in the ASD group, the lack of association of these changes (and indeed the composite measure, mean diffusivity) with the maturing M50 latency suggests that the WM maturation processes indexed by these DTI parameters are indeed atypical in ASD.

WM diffusion anisotropy and electrophysiological auditory cortex responses mature across development, with greater fractional anisotropy and earlier auditory latencies in older individuals. Individuals with ASD showed aberrant WM development as well as delays in the M50 response. A strong correlation between diffusion fractional anisotropy and M50 latency was observed only in the TD group, suggesting that WM maturation facilitates the conduction of electrical impulses to achieve more efficient and rapid electrophysiological activity. Although a loss of a WM structure and auditory cortex function relationship was observed in individuals with ASD, M50 latency did decrease as a function of age in ASD, although systematically delayed compared to age-matched typically-developing controls. Thus, factors other than white matter conduction velocity impact the auditory evoked response, and at least some of these factors do not exhibit an atypical developmental trajectory in ASD.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for screening for a therapy against an autism spectrum disorder, said method comprising:
   a) administering a therapy to a subject;
   b) measuring brain activity in said subject by magnetoencephalography after administering an audio stimulus to the subject and measuring the 50 ms response; and
   c) comparing the delay in the 50 ms response in the subject compared to a baseline of the subject,
   wherein a decrease in the delay in the 50 ms response in said subject compared to the baseline of the subject indicates that the therapy is effective against said autism spectrum disorder.

2. The method of claim 1, further comprising determining the baseline of the subject by measuring brain activity in said subject by magnetoencephalography after administering an audio stimulus to the subject prior to the administration of the therapy.

3. The method of claim 1, wherein said therapy is a compound.

4. The method of claim 3, wherein said compound is a small molecule.

5. The method of claim 1, wherein said therapy is a non-pharmacological intervention.

6. The method of claim 1, wherein the measurement of the 50 ms response is collapsed across hemispheres.

7. A method for determining whether a subject would be responsive to a therapy against an autism spectrum disorder, said method comprising:
   a) administering a therapy to a subject;
   b) measuring brain activity in said subject by magnetoencephalography after administering an audio stimulus to the subject and measuring the 50 ms response; and
   c) comparing the delay in the 50 ms response in the subject compared to a baseline of the subject,
   wherein a decrease in the delay in the 50 ms response in said subject compared to the baseline of the subject indicates that said subject is responsive to the therapy.

8. The method of claim 7, further comprising determining the baseline of the subject by measuring brain activity in said subject by magnetoencephalography after administering an audio stimulus to the subject prior to the administration of the therapy.

9. The method of claim 7, wherein said therapy is a compound.

10. The method of claim 9, wherein said compound is a small molecule.

11. The method of claim 10, wherein said small molecule is arbaclofen.

12. The method of claim 7, wherein said therapy is a non-pharmacological intervention.

13. The method of claim 7, wherein said subject is determined to be acceptable for inclusion in a drug trial.

14. The method of claim 7, wherein the measurement of the 50 ms response is collapsed across hemispheres.

* * * * *